(12) United States Patent
Sun (10) Patent No.: US 7,812,622 B1
(45) Date of Patent: Oct. 12, 2010

(54) SENSOR AND METHOD FOR DETECTING ANALYTES IN FLUIDS

(76) Inventor: Yizhong Sun, 30152 Galbreth Ct., Castaic, CA (US) 91384

( * ) Notice: Subject to any disclaimer, the term of this patent is extended or adjusted under 35 U.S.C. 154(b) by 0 days.

(21) Appl. No.: 12/217,644

(22) Filed: Jul. 8, 2008

Related U.S. Application Data (63) Continuation of application No. 10/238,794, filed on Sep. 9, 2002, now Pat. No. 7,465,425.

(51) Int. Cl.
*G01R 27/08* (2006.01)
*G01R 27/26* (2006.01)
*G01R 27/02* (2006.01)

(52) U.S. Cl. .................. 324/707; 324/439; 324/674; 324/681; 324/686

(58) Field of Classification Search .......... 324/684
See application file for complete search history.

(56) References Cited

U.S. PATENT DOCUMENTS

| | | | | |
|---|---|---|---|---|
| 4,795,968 A * | 1/1989 | Madou et al. | ............... | 324/674 |
| 4,864,462 A * | 9/1989 | Madou et al. | ............... | 324/663 |
| 4,887,455 A * | 12/1989 | Payne et al. | ................. | 324/722 |
| 5,494,831 A * | 2/1996 | Kindler | .................... | 205/777.5 |
| 5,571,401 A * | 11/1996 | Lewis et al. | .................. | 205/787 |
| 5,846,744 A * | 12/1998 | Athey et al. | ................... | 435/7.9 |
| 6,200,444 B1 * | 3/2001 | Ahlers et al. | ................ | 204/418 |
| 6,300,123 B1 * | 10/2001 | Vadgama et al. | ......... | 435/287.1 |
| 6,319,724 B1 * | 11/2001 | Lewis et al. | .................. | 436/149 |
| 6,374,662 B1 * | 4/2002 | Oda et al. | .................... | 73/23.34 |
| 6,387,329 B1 * | 5/2002 | Lewis et al. | .................... | 422/98 |
| 6,566,894 B2 * | 5/2003 | Rump | ......................... | 324/681 |
| 6,631,333 B1 * | 10/2003 | Lewis et al. | .................... | 702/24 |
| 6,809,462 B2 * | 10/2004 | Pelrine et al. | ............... | 310/319 |
| 6,895,803 B2 * | 5/2005 | Seakins et al. | ............. | 73/29.02 |
| 7,097,973 B1 * | 8/2006 | Zenhausern | .................... | 435/6 |

* cited by examiner

*Primary Examiner*—Timothy J Dole
(74) *Attorney, Agent, or Firm*—Thomas I. Rozsa

(57) ABSTRACT

A fluid sensor is constructed to have a pair of electrodes whereas between electrodes there are not additional materials designated to adsorb analytes if their concentrations are high, or there are adsorbents if the analyte concentrations are low. An alternating current voltage of varying frequencies is applied to the electrodes of the sensor by an alternating current device. In return, it detects electrical properties such as impedance and its components, reactance, resistance, and phase angles of the sensor with analytes whereas the analytes reside in or pass through the electrodes at each frequency. Thus a spectrum of electrical properties of the analyte can be established at various applied frequencies. The electrical properties are analyzed by a pattern recognition process, and compared with those of the known fluids. Therefore, the fluid can be detected and identified. A reference sensor is provided with the same configuration of the fluid sensor. With combining electrical signals from the fluid sensor and reference sensor, the present invention brings a number of advantages, including elimination of humidity influence, polymer film aging effect, and effect of temperature variations. In addition, a temperature programming is suggested in the present invention to better control processes of adsorption and desorption for analytes thus the analytes can be better detected and identified.

26 Claims, 4 Drawing Sheets

SENSOR AND METHOD FOR DETECTING ANALYTES IN FLUIDS

This application is a Continuation of application Ser. No. 10/238,794 filed on Sep. 9, 2002 which is now U.S. Pat. No. 7,465,425.

BACKGROUND OF THE INVENTION

1. Field of the Invention

The present invention relates generally to the field of sensors, and more particularly relates to sensors for detecting analytes in fluids.

2. Description of the Prior Art

Sensors are widely used in technologies of detecting the presence of analytes in fluids. The following references are pertinent to this field of art:
1. U.S. Pat. No. 4,887,455 issued on Dec. 19, 1989 to Payne et al. for "Gas Sensor" (hereafter "the Payne '455 patent");
2. U.S. Pat. No. 5,571,401 issued on Nov. 5, 1996 to Lewis et al. for "Sensor Arrays for Detecting Analytes in Fluids" (hereafter "the '401 Lewis patent");
3. U.S. Pat. No. 6,319,724 issued on Nov. 20, 2001 to Lewis et al. for "Trace Level Detection of Analytes Using Artificial Olfactometry" (hereafter "the '724 Lewis patent"); and
4. Payne, et al., "High-Frequency Measurements of Conducting Polymers: Development of A New Technique for Sensing Volatile Chemicals", Meas. Sci. Technol. 6 (1995) pp. 1500-1507 (hereafter "the Payne Publication"); and
5. U.S. Pat. No. 7,465,425 issued on Dec. 16, 2008 to Sun for "Sensor And Method For Detecting Analytes In Fluids" (hereafter "the Sun '425 patent").

The Payne '455 patent discloses a gas sensor that has a semiconductor organic polymer layer exposed to a gas to be detected. An analyzer applies an alternating electric signal at specific resonant frequencies to the sensor to detect the change in the sensor's impedance characteristics which is compared by a microcomputer with reference characteristics stored in a memory of the microcomputer. The gas in contact with the sensor can be detected because of the resulting difference spectra. The patent further discloses that the best performance of the invention is likely to be conducted between frequency ranging 100 MHz to 500 MHz wherein the resonance may happen.

The '401 Lewis patent discloses arrays of chemical sensors for detecting analytes in fluids. The sensors include first and second conductive elements electrically coupled to and separated by a chemically sensitive resistor which provides an electrical path between the conductive elements. The resistor includes a plurality of alternating nonconductive regions made of a nonconductive organic polymer and conductive regions made of a conductive material transverse to the electrical path. The resistor further provides a difference in resistance between the conductive elements when contacted with a fluid containing a chemical analyte at a first concentration, and then at a second different concentration. Arrays of such sensors are constructed with at least two sensors having different chemically sensitive resistors providing dissimilar such differences in resistance. Variability in chemical sensitivity from sensor to sensor is provided by qualitatively or quantitatively varying the composition of the conductive and/ or nonconductive regions. An "electronic nose" for detecting an analyte in a fluid may be constructed by using such arrays in conjunction with an electrical measuring device electrically connected to the conductive elements of each sensor.

The '724 Lewis patent discloses a method using artificial olfactometry for detecting the presence of an analyte indicative of various medical conditions, including halitosis, periodontal disease and other diseases.

The Payne Publication discloses the change in the alternating current (AC) impedance characteristics of poly-N-(2-pyridyl) pyrrole in the presence of different volatile chemicals.

It can be seen from the above cited references that significant efforts have been devoted in the past in the research and development of sensors that are capable for detecting and identifying analytes in fluids. Identification of analytes in fluids from instrumental analysis is accomplished from mimic mechanisms of the mammalian olfactory system that applies probabilistic repertoires of many different receptors to record a single odorant.

However, identification of the odorant is dependent upon not only the results from highly specific receptors but also the output from less specific ones. In other words, identification is based on recognition a spectrum of signals that resemble a specific pattern. Following this direction, conventional technologies in sensor configuration were developed according to the following two schemes to generate a signal spectrum: applying multiple sensor and single sensor strategies.

In the approaches that utilize multiple sensors, various detecting devices have been developed that use metal oxide thin film resistor sensors, conductive polymer or polymer carbon powder composite film chemi-resistor sensors, polymer coated quartz crystal microbalance (QCM) sensors, polymer coated surface acoustic wave (SAW) sensors, metal-oxide-silicon field-effect-transistor (MOSFET) sensors, and optical sensors. However, although much progress has been made in the past, there are still primary disadvantages inherited from the sensing mechanisms of such multi-sensor technologies. The disadvantages include the requirement of a large number of sensors to generate a patterned information, the sophistication required for the sensor configuration, the poor reproducibility in sensor manufacturing, the strong humidity influence on chemical analysis, the slow response, the expensive electronics equipment required, and the very restricted operating conditions.

Various polymer films with a general thickness of several micrometers have been extensively used in multi-sensor configurations to improve sensor sensitivity and detection limit. This is primarily due to the fact that the polymer films can trap the chemical vapors because of their specific chemical selectivities on analytes. As a result, the analytes will be concentrated inside of the polymer prior to detection.

However, the conventional polymer films also inherit a number of disadvantages. First, the thin films of polymer are sensitive to the humidity associated with the analyte. Humidity is the predominant factor to influence performance of the polymer film based gas sensors. Second, polymer films have an aging effect that affects the sensor stability for long term operations. Third, it is difficult to achieve reproducibility of dispensing the polymer films onto sensors, particularly when a large number of sensors must be used in a multi-sensor configuration.

In the approaches that utilize a single sensor strategy, various instruments have been developed that are based on the mechanisms of gas chromatography (GC), mass spectrometry (MS), and light spectrum. Generally, these instruments are very expensive. Moreover, they are typically very bulky in sizes that makes miniaturization almost impossible. As a result, they are less attractive in the market where portability of instrument becomes increasingly important.

As an example, the Payne Patent and Publication discussed above disclose application of a single sensor for detecting impedance and phase sensitive components of conductive polymer modified electrodes at various frequencies to establish a spectrum of signals. However, the Payne device requires high frequencies ranging from 100 MHz to 500 MHz, which brings significant difficulties in instrument manufacturing and application. In addition, it still has the disadvantages inherent from polymer films.

In order to overcome deficiencies of the Payne technology and invent a new single sensor applying frequency sweeping, the '425 Sun patent discloses a single sensor as an analytical sensor for detecting analytes in fluids. The sensor is constructed from applying a pair of electrodes, wherein between the electrodes there are no additional materials designated to adsorb analytes, if their concentrations are high, or there are adsorbents, if the analyte concentrations are low. An alternating current voltage of varying frequencies is applied to the sensor by an alternating current device. In return, it detects electrical properties such as impedance and its components, reactance, resistance, and phase angles of the sensor with the analytes in fluids when they reside in or pass through the electrodes at each frequency. Thus two spectra of electrical properties of the analyte can be established at various applied frequencies from a single measurement. The electrical properties are analyzed by a pattern recognition process, and compared with those of the known Objects. Therefore, the analyte can be detected and identified. A reference sensor is provided with the same configuration of the analytical sensor. By combining electrical properties from the analytical and reference sensors, the '425 Sun patent provides a number of advantages, including elimination of humidity influence, polymer film aging effect, and electrical property variations caused by the temperature variations.

Therefore, it is desirable to design and develop a new sensor and method that overcome the disadvantages of conventional sensor devices, and have a better reproducibility of performance and sensor manufacturing, fewer interference deficiency, enhanced sensitivity, less restricted operation conditions, and increased portability.

SUMMARY OF THE INVENTION

The present invention is directed to a sensor and related method for detecting analytes in fluids.

It is an object of the present invention to provide a new and unique sensor device and technique for detecting analytes in fluids that utilizes a single sensor design for analyzing AC electrical information of the analytes at various selected frequencies ranging from 10 KHz to 1 MHz.

It is also an object of the present invention to provide a new and unique sensor device and technique for detecting analytes in fluids that can identify an analyte by comparing a single pattern of the AC electrical information of the analyte at various selected frequencies ranging from 10 KHz to 1 MHz with patterns of electrical information of known analytes.

It is another object of the present invention to provide a new and unique sensor device and technique for detecting analytes in fluids that has a background reference mechanism to reduce the background influence, including humidity, on the analyte detection.

It is a further object of the present invention to provide a new and unique sensor device and technique for detecting analytes in fluids that employs temperature programming on regulating the sensor temperature to improve the performance of the analyte detection.

It is the further object of the present invention to provide a new and unique sensor device and technique for detecting analytes in fluids that has capability for applying all types of organic, inorganic, and metal adsorbents to selectively analyze analytes including small molecule chemicals.

It is an additional object of the present invention to provide a new and unique sensor device for detecting analytes in fluids that is compact in size, portable, easy to use, inexpensive to produce, and low in energy consumption.

In a preferred embodiment of the present invention, a novel and unique detection method and device are provided for identifying analytes in fluids, which are based on detecting AC electrical properties of the analytes such as impedance and its components, i.e., resistance and reactance, as they are governed by chemical characteristics of the analytes. The present invention utilizes a single sensor that has a pair of metal conductors to analyze AC electrical information of the analytes at various frequencies ranging from 10 KHz to 1 MHz.

The measurement results in a patterned AC electrical information for the analytes at the applied frequencies. After analyzing the AC electric information at various selected frequencies through a pattern recognition procedure, the analytes can be identified by comparison with patterns of electrical information of known analytes.

In the present invention method, the identification of chemicals is based on generating patterns of characteristic information gathered from the chemicals in the analytes being tested, which information are specific to the chemicals and are gathered from various dimensions. Therefore, the present invention method is focused on finding such specific characteristic information that is related to the natural characteristics of the chemicals. For example, dielectric constant is one of the natural characteristics of chemicals, and can be used to identify chemicals. The dielectric constant can be measured electrically by the capacitive reactance in impedance complex in the vector domain. Hence capacitive reactance is one of the characteristic information useful for identifying chemicals (in the scalar domain, capacitance is proportional to the dielectric constant and has been used for identifying chemicals).

In addition, each chemical has its unique composition of chemical elements which results in specific chemical characteristics. Such characteristics may be measured by resistance. For example, volatile organic chemical rich in hydrogen and oxygen changes electric conductivity (resistivity) of metal oxide based sensors.

Since chemicals in pure form (including their gas phases) are not electrically conductive, capacitive reactance is the dominant component in impedance comparing with resistance. However, although resistance value is small, it reflects resistive characteristics of chemicals and describes their properties in another dimension. Therefore, resistance information is also important for identifying chemicals.

Impedance can be obtained applying Ohm's law in AC condition:

$$Z=V/I \quad [1]$$

where Z is the impedance vector, V is the voltage vector, and I is the current vector. It can be understood that from the above equation, the voltage across the sensor is proportional to the impedance under a constant current technique. Current passing through the sensor electrodes is reverse proportional to the impedance applying a constant voltage technology. Therefore, as alternatives, either current or voltage may be used (in the place of impedance) for identification purpose.

The present invention sensor and method does not require additional materials for adsorbing chemical vapors between the metal conductors in the sensor design when the analytes are sufficiently concentrated. When the analyte concentrations are low, the present invention sensor and method has the option of using adsorbent materials in the sensor design to improve the sensitivity and detection limit of the sensor.

The present invention has many novel and unique features and advantages. In summary, the present invention sensor and method for detecting analytes in fluids utilize a single sensor design operating within a frequency range of under 1 MHz which results in an easy instrument design and application. It does not require the use of a conductive polymer film in the sensor structure and has capability to apply all types of adsorbents. It further provides a background reference and has a low energy consumption that allows the use of a temperature programming to more precisely control the processes of adsorption and desorption for analytes, which improves the detection and identification of the analytes. In addition, the present invention sensor device has a low cost to manufacture and is compact in size which makes it portable and easy to use.

It is noted that one of the main advantages of the present invention is to use single sensor configuration for generating a spectrum of chemical signals. The reproducibility of manufacturing sensors can be easily achieved with a single sensor strategy when a few pairs of identical sensors are needed for an instrument. The small size of the sensor which results in low power consumption for controlling sensor temperature and small volume requirement also allows the implementation of a dual sensing detection strategy which, in addition to an analytical sensor, incorporates a reference sensor with the identical configurations as that of the analytical sensor.

With this dual sensor configuration, samples of an analyte with background subjects such as humidity levels are tested by the analytical sensor while only the background subjects are tested by the reference sensor. By comparing the outputs from the analytical and reference sensors, the background effect can be removed from the test result of the sample analyte. Similarly, the aging effect for polymer film based sensors, and changes in testing responses induced by temperature variations, can also be removed or eliminated.

These and further novel features and objects of the present invention will become more apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 4A shows the dual sensor configuration 12 without an integrated form of two sensors;

FIG. 4B shows an integrated form 13;

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figures 3, 4A, 4B:
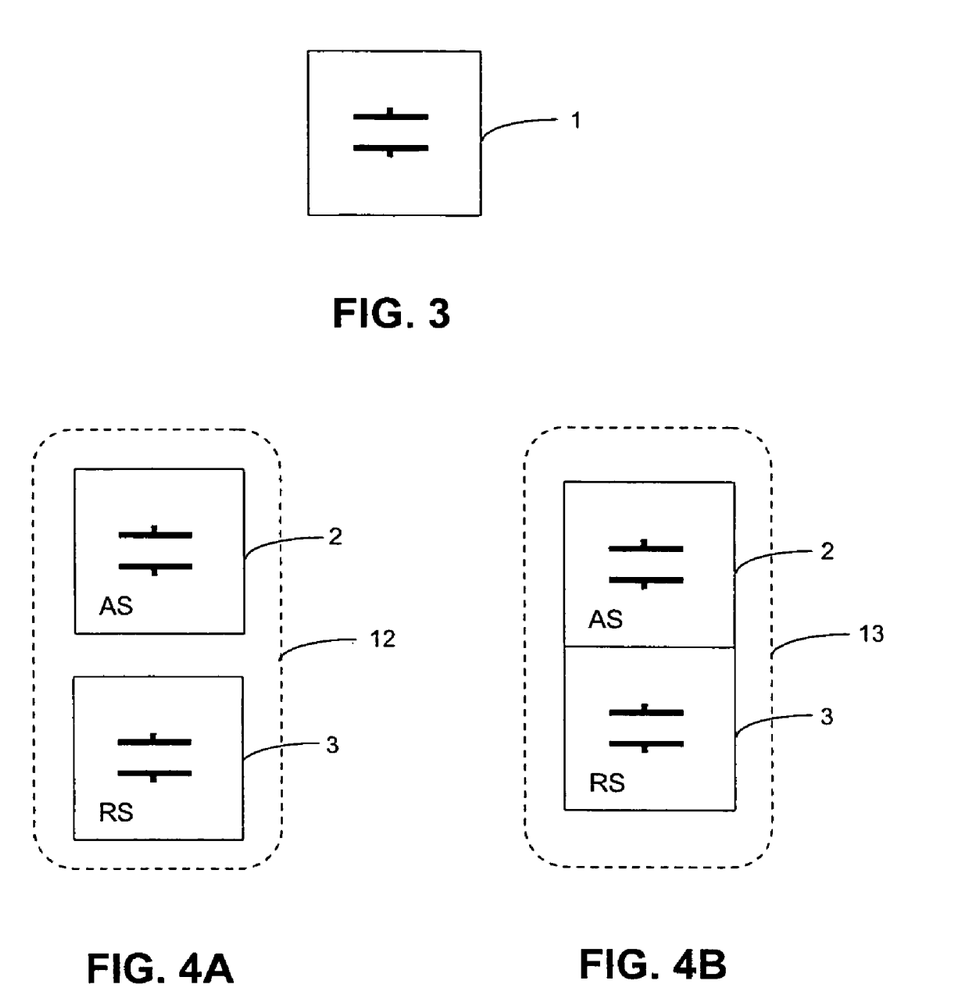
FIG. 3 illustrates a schematic diagram of a single sensor 1 containing a pair of metal wires or plates acting as electrodes or a capacitor.
FIG. 4A shows a dual sensor configuration which utilizes two identical sensors 1, one as an analytical sensor 2 (AS in abbreviation), and the other as a reference sensor 3 (RS).
FIG. 4B shows a dual sensor configuration which utilizes two identical sensors, one as an analytical sensor 2, and the other as a reference sensor 3.

Referring to FIGS. 3, 4A, 4B and 5, the present invention sensor and method for detecting and identifying analytes in fluids have two main objectives. Referring to FIG. 3, the first major objective of the present invention is to use a single sensor configuration 1 for effective identification of analyte by detecting certain electrical properties associated with its distinguished physical and chemical characteristics, such as dielectric constant, element electronegativity, and polarity. This first main objective of the present invention is achieved by applying an impedance spectroscopy with frequency sweeping technique. With a frequency sweeping, a pattern of information is constructed at various selected frequencies. By analyzing the information with a pattern recognition process, the analytes can be identified in comparison with those of known substances. The second main objective of the present invention is to provide a method that can eliminate effect of background subjects, such as humidity, which influence the analysis of analytes. Referring to FIGS. 4A and 4B, the second main objective is achieved by applying a dual sensing configuration which utilizes two identical sensors 1, one as an analytical sensor 2 and the other as a reference sensor 3.

It should be indicated that implementation of the dual sensing strategy is practically applicable in the present invention due to the advantage of small volume requirement from applying the single analytical sensor to obtain the patterned information for the analytes.

Gases and volatile chemicals have their distinguished dielectric constants. They also contain various chemical elements that have their distinguished values of electronegativities. In addition, in terms of molecular symmetry, gases and volatile chemicals have their unique molecular sizes and shapes. These factors determine characteristics for chemical analytes in their adsorption and desorption processes.

Figure 5:
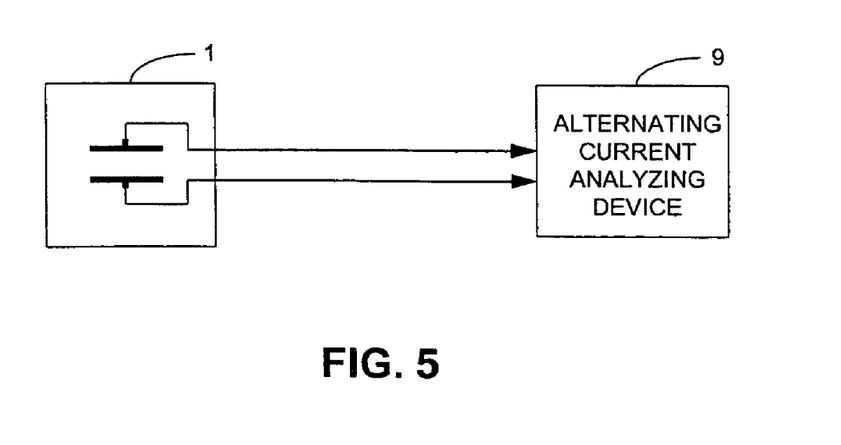
FIG. 5 shows a diagram for electrically connecting a single sensor 1 to an alternating current analyzing device 9.

These physical and chemical characteristics can be described with certain AC electric properties, such as impedance Z and its phase sensitive components: reactance X, resistance R, and phase angle θ, as the analyte is under an AC voltage excitation. Referring to FIG. 5, the AC electric properties can be obtained by using an instrument of impedance analyzer or other known alternating current devices 9. In its simplest form, a test device can be a pair of metal wires or plates acting as electrodes or a capacitor. The AC electric properties of the gases or chemical vapors are obtained as gases or chemical vapors reside or pass through the electrodes or capacitor.

Impedance is described as $$Z = R + X \quad [2]$$

in complex (with the bold letters indicating vectors). The phase angel θ can be calculated from the R and X values.

Reactance X of the sensor electrodes in the present invention is combined with a reactive capacitance $X_C$, and reactive inductance $X_L$, which can be described as follows:

$$X_C = j(-1/2\pi fC) \quad [3]$$

$$X_L = j(2\pi fL) \quad [4]$$

where C is a capacitance that is proportional to a dielectric constant of the medium residing between electrodes, and L is the inductance of the electrode. For a small electrode, the value of inductance L is small and the reactance X is predominantly capacitive.

If in the absence of analyte the reactive capacitance is $X_C(1)$, and in the presence of the analyte the reactive capacitance is $X_C(2)$, then their difference $\Delta X_C$:

$$\Delta X_C = X_C(2) - X_C(1) \quad [5]$$

can be obtained, which is the change of reactive capacitance as the result of the presence of the analyte.

Since the capacitance of analyte is determined by its dielectric constant, reactive capacitance can be used to detect and identify the analyte. This means reactive capacitance provides a signature information of each chemical. By varying the frequencies, the present invention is able to construct a reactance spectrum to record electrical property of the analyte at each frequency. This results in obtaining patterned chemical characteristics of the analyte.

Gases and chemical vapors will be adsorbed by the surface of the test device. This capability creates a complicated diffusive process, and surface interfacial kinetics or surface resistance for the analytes, which are associated with their distinguished molecular characteristics. For example, exposure to hydrogen or oxygen-rich of volatile organic compounds noticeably changes the electrical conductivity of metal oxide sensors.

Since oxygen or hydrogen has its defined electronegativity, the changing of conductivity (resistivity) indicates that resistance can be used to record chemical characteristics of vapors.

In the present invention, a series of resistance information is also generated with varying frequencies. The change of resistance can be defined as:

$$\Delta R = R(2) - R(1) \quad [6]$$

where $R(1)$ is the resistance of electrode substrate in the absence of any analyte and $R(2)$ is the resistance of substrate exposed to the analyte.

Comparing magnitude of resistance and reactance, it is noted that reactance is the predominant factor to govern values of impedance since chemicals are not conducting at their dry phases. It is also noted that phase angles θ can be calculated from values of R and X. Therefore, the change of phase angle θ is also readily available. Combining the information of change of reactive capacitance and resistance and/or change of phase angles, a matrix of electrical properties is constructed that contains chemical characteristics of the analytes at various selected frequencies.

As the change of electrical property varies nonlinearly with frequency, the variation of the electrical property change can be analyzed through a pattern recognition process including applications of multivariate analysis method. Applying such pattern recognition analysis on the matrix of electrical property, the chemical characteristics can be identified.

As a result, the analyte can be differentiated by comparing the patterned chemical characteristics of the analyte with those of known substance.

The preferred frequency range of the present invention method is from 10 KHz to 1 MHz. Applying the various selected frequencies can not only identify the analytes but also increases the options of instrument design and practical application.

The present invention sensor design does not require the use of any conductive polymer film for identifying analytes at high concentration. This is because the AC voltages can be applied across the vacuum between the two electrodes without conductive materials placed in between. This is well suitable to be used as a detection method of gas chromatography where the analyte vapor is separated and concentrated in the chromatographic process. This new detection method will provide information on not only the quantities but also the identities of the analytes in gas chromatography.

Figure 6:
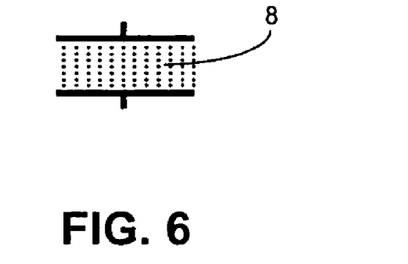
FIG. 6 shows a schematic of any type of adsorbent 8 placed onto electrodes or a capacitor for adsorbing an analyte from a fluid.

In addition, referring to FIG. 6, since AC signal can travel through vacuum, the present invention can use any type of adsorbents 8 whether or not they are electrically conductive for detecting analytes to concentrate or selectively concentrate their dilute vapors. Therefore, the present invention method can utilize a variety of developed techniques on concentrating chemicals or selectively concentrating marker gases of analytes in fluids for dilute analytes to improve sensitivity and selectivity of the sensor. Such techniques typically involve polymer films, polymer inorganic material composites, composites containing palladium, solid inorganic materials used as stationary phase in adsorption chromatography, and polymeric materials used as stationary phase in preparation of packed column in gas partition chromatography.

For example, hydrogen is an important industrial gas for many applications. It is often critical to detect and identify the hydrogen gas due to safety concerns. In the present invention, the hydrogen gas can be selectively concentrated by applying composites containing palladium particles, and organic or inorganic fillers. This is because the hydrogen gas has a large solubility in the palladium metal (often referred to as a "hydrogen sinker"). Since the present invention analyte detection method is not limited to adsorbent materials that are electrically conductive, it has a great flexibility to choose any percentage of palladium particles in the composite to meet the conditions of required hydrogen gas concentrations in analytes for the application of the present invention.

Furthermore, adsorption chromatography uses solid particles as stationary phase to selectively adsorb molecules. Various solid inorganic materials can be used for this purpose.

Among them, molecular sieves, silica gel, alumina, porous carbon particles, and calcium carbonate are the most popular choices.

For example, molecular sieves retain adsorbates by strong physical forces, and separate molecules based on their sizes, configurations, polarities, and degrees of unsaturation. Molecular sieves will adsorb carbon monoxide in preference to argon. They preferentially adsorb polar molecules containing oxygen, sulfur, chlorine, or nitrogen atoms, and asymmetrical molecules containing oxygen, sulfur, chlorine, or nitrogen atoms, and asymmetrical molecules. Molecular sieves also effectively trap ethylene or propylene from saturated hydrocarbons.

In gas partition chromatography (GC), separation of chemicals in mixture is based on vapor pressure of chemicals and selective interactions between chemicals and polymeric materials used as the stationary phase of the GC columns. The stationary phase materials are coated onto solid support substance. At the molecular level, the interaction is based on intermolecular forces between chemicals and materials of the stationary phase such as dispersion, induction, orientation, and donor-acceptor interaction. To help the understanding of the processes described above, the term "like dissolves like" may be useful to explain results of such intermolecular interactions. Selectivity is one of results of the interaction due to a similarity between "likeness" of a kind of chemicals and materials of the stationary phase of the column. For example, polarities are physical parameters of chemicals and can be used to describe such likeness. Polar chemicals like polar materials of the stationary phase, and non polar chemicals go to non polar stationary phase.

Based on this principle, objective of selective partition of a type of chemicals can be achieved by using a kind of stationary phase materials whose polarities are close or match the polarities of the chemicals. For example, polysiloxane is a non polar material. It is most popularly used as the base materials of the GC stationary phase since its basic chemical structure can be readily derived by methyl, vinyl, phenyl, diphenyl, 3,3,3-trifluoropropyl, 2-cyanoethyl, or 3-cyanopropyl constituents to change its polarity from non polar to polar. Therefore, specifically derived polysiloxane polymers are appropriate to many types of industrial chemicals in terms of closeness of their polarities.

The following polymers are often involved in applications for the industrial chemicals in fluid:

1. Poly(100% dimethylsiloxane) for analytes of solvents, petroleum products, fuel, oil, hydrocarbons, pharmaceuticals, flavors, and fragrances.

2. Polymers containing (5% diphenyl/95% dimethyl), or (35% diphenyl/65% dimentyl), or (14% cyanopropyl/86% dimethyl) for analytes of pesticides, aromatic hydrocarbons, polychlorinated biphenyl, oxygenates, amines, essential oil, pharmaceuticals, environmental samples, and nitrogen containing herbicides.

3. Poly(20% diphenyl/80% dimethylsiloxane) for flavor aromatics and alcoholic beverage.

4. Polymers containing (50% phenyl/50% methyl) or (trifluoropropylmethyl) for environmental chemicals, solvents, and ketones.

5. Ploy(65% diphenyl/35% dimethylsiloxane) for analytes of phenols and fatty acids.

6. Poly(50% cyanopropylmethyl/50% phenylmethylsiloxane) for analytes of carbohydrates and neutral sterols.

The derived polysiloxane polymers can be coated onto solid support particles for preparation of packed columns. The solid support can be porous ceramics including alumina, silica, and glass, or other particles.

Applying a single sensor with electric frequency sweeping technique, the present invention is able to not only obtain a patterned information of analyte but also gain a distinctive advantage of having small sized sensor and sensor compartment in sensor design. The small sized sensor and sensor compartment make the present invention practically be able to utilize a dual sensing detection in sensor manufacturing, particularly for manufacturing handheld and battery powered electronic nose instrument.

The present invention applies two identical sensors one serving as an analytical sensor, and the other as a reference sensor. When background subjects such as humidity is a critical factor that affects sensor performance, the analytes with background subjects are tested with the analytical sensor, but only the background subjects are tested with the reference sensor. By subtracting electrical property of the analytical sensor from that of the reference sensor, the influence of background subjects, including humidity, can be eliminated.

One application of the this dual sensor arrangement is for in situ medical diagnostic applications, for example detecting ear and mouth diseases for patients. In such applications, the analytes of chemical vapor generated by bacteria caused by diseases are overlapped by the humidity in breath where the water concentration in humidity is significantly higher than that of the analytes. By using a reference sensor, the humidity can be measured by the reference sensor and its electrical properties can be subtracted from the electrical properties of the analytical sensor which measures both the analytes and the humidity level. As a result, the information of the analytes can be obtained without the error introduced by the humidity level. Similarly, this dual sensor arrangement of the present invention can also be used to compensate the polymer film aging effect, or influence caused by temperature variations.

Gases and chemical vapors will be influenced by temperature in their adsorption and desorption process. In gas chromatography, a temperature programming process is often applied for efficient separation of chemical mixture. Because of the small sized sensor and sensor compartment which result in low power consumption for temperature regulation on sensor and analyte, the present invention can utilize temperature programming to control adsorption and desorption process on gases and chemical vapors in their interaction with sensor electrodes. This makes it possible that chemical characteristics of the analytes can be fully explored by the present invention method.

The present invention enables the design and development of sensor instrument with a small size, low cost and great portability. As an example, the present invention sensor is well suitable for a disposable electrode configuration in design of electronic nose instrument.

EXAMPLES

The following are examples and experimental information of the present invention sensor and method which are offered by way of illustration only and not by way of limitation.

A pair of electrodes were constructed with gold wires. The electrodes were 12 mm in length and had a gap up to 1 mm. The electrodes were connected to an instrument of impedance analyzer, such as an "Agilent 4294A" analyzer. Calibration of electrodes was proceeded prior to sample measurement. A frequency sweeping method was used in impedance measurement where resistance and reactance or impedance and phase angle could be simultaneously obtained at various frequencies within the swept frequency range.

Five chemicals were used in impedance tests, including acetone, acetic acid, hexane, toluene, and water. In the experiment, each chemical was alternatively measured six times. In doing so, each chemical was filled a half full into six vials, which were tightly sealed except for sample testing.

Before measuring each chemical sample, room air was first measured and recorded, and its impedance, resistance, and reactance were used as references. To measure a sample, a vial containing such sample was unsealed and placed where the liquid surface was close to the electrodes. A cotton ball was used to block a joint area of electrode cable and vial opening to prevent variation of chemical vapor concentration inside the vial. Then a waiting period of ten seconds were applied before taking the impedance data. After the measurement was done, the vial was immediately taken away from the electrodes and resealed. The measured vial was not reused.

The electrodes were then exposed to room air again for about ten minutes before the next measurement. The sequence of measuring chemicals was in the order of toluene, acetone, hexane, water, and acetic acid. The second and subsequent (up to the sixth) measurements were taken with the same sequence. Change of electrical property is obtained from the following equation:

$$\text{Change of electrical property} = \text{Electrical property of sample} - \text{Electrical property of air} \quad [7]$$

Thus a raw data matrix was constructed from measuring each chemical at various frequencies, wherein each two columns represented resistance change and reactance change at one frequency, respectively, and each row represented a single measurement of a chemical.

Figure 1:
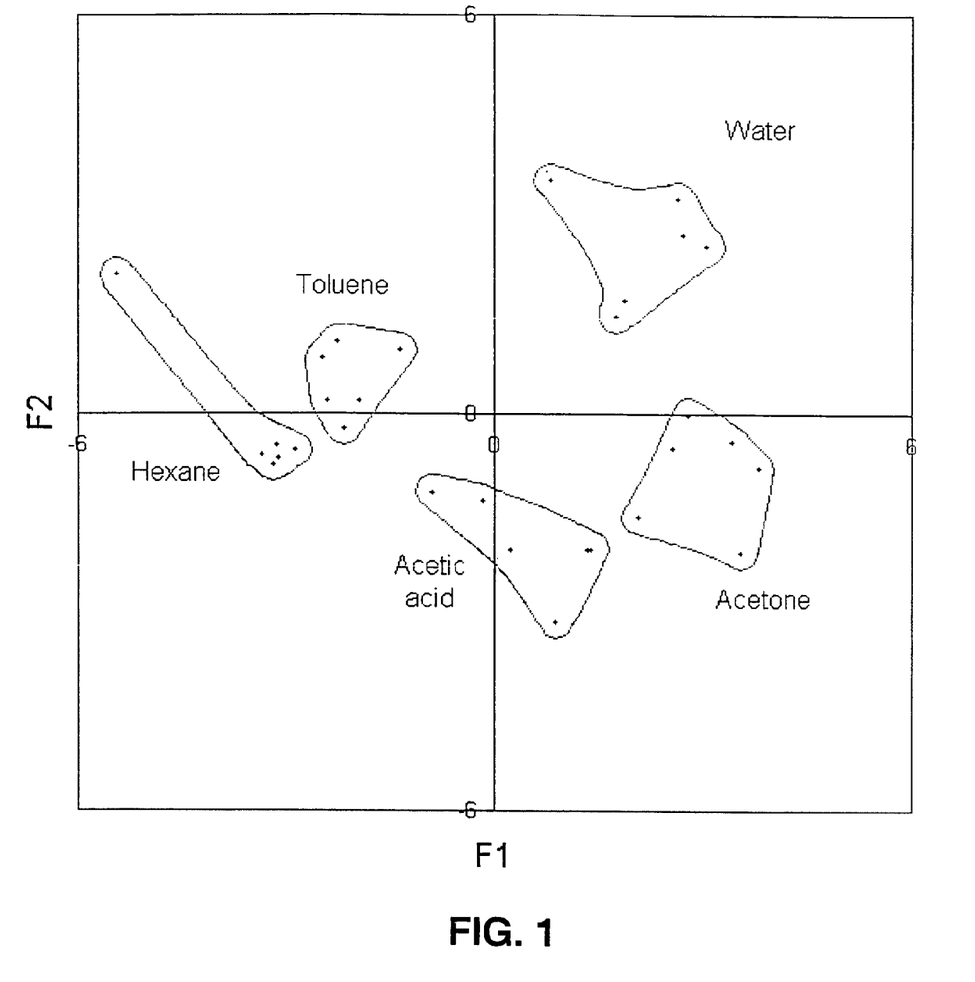
FIG. 1 is an illustrative plot diagram showing the result of classification for five (5) chemicals from a principal component analysis, where resistance and reactance at seven (7) frequencies within a range of 10 KHz to 500 KHz are used in the analysis.

Referring to FIG. 1, there is shown the principal component analysis (PCA) for chemicals of acetic acid, acetone, hexane, toluene, and water with their resistance and reactance data obtained at 10, 20, 50, 100, 200, 300 and 500 KHz. The electrical information of the chemicals is simplified after applying principal component analysis and presented in accordance with two principal components F1 and F2. During data analysis applying PCA, the raw data of change of resistance and reactance in the matrix was autoscaled and normalized to the length one before further processing. It is clear from the graph that the test results from the same chemical are grouped in a particular area, as the 5 chemicals are separated and located in different areas of the F1 and F2 plane. The results of principal component plotting indicate that chemicals can be distinguished with their electrical properties, such as impedance and its phase sensitive components (i.e., resistance and reactance) obtained from frequency ranging from 10 KHz to 500 KHz.

Figure 2:
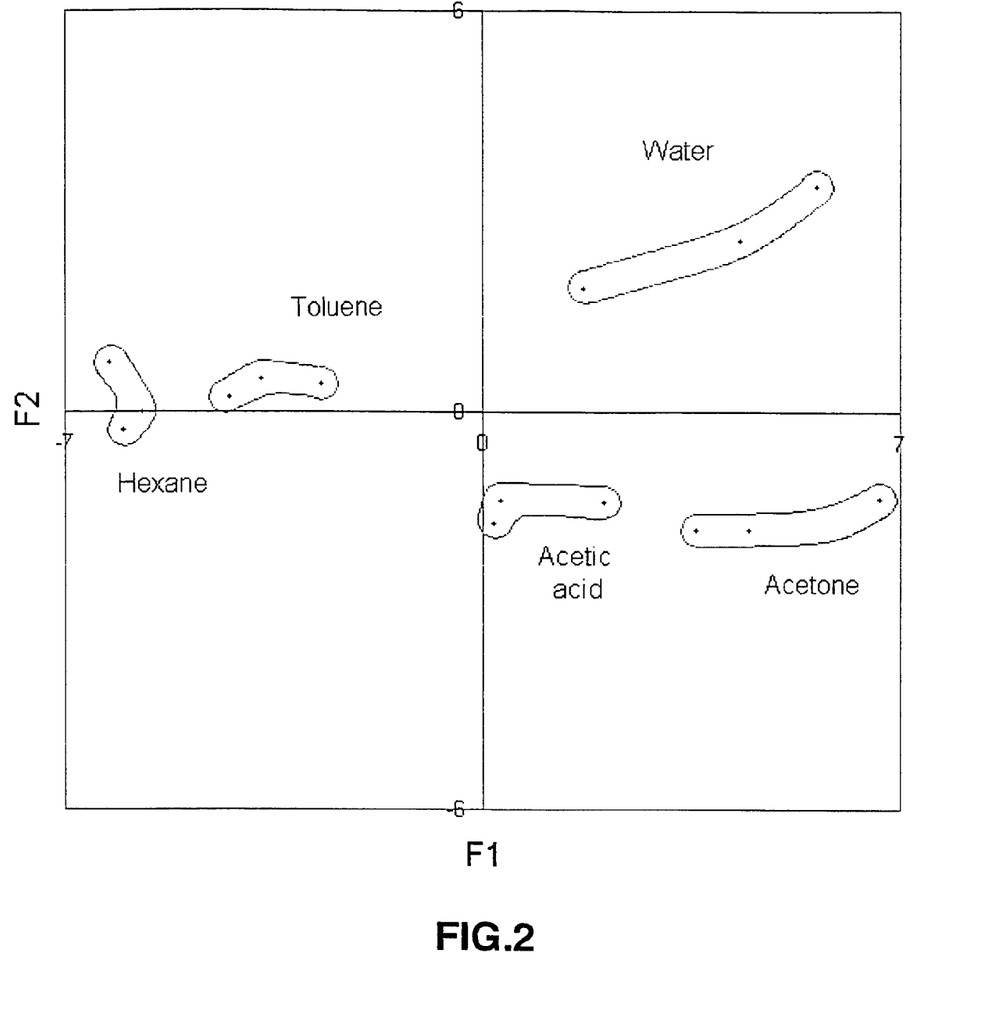
FIG. 2 is an illustrative plot diagram showing the result of classification for five (5) chemicals from the principal component analysis, where resistance and reactance at eleven (11) frequencies within a range of 500 KHz to 1000 KHz are used in the analysis.

Referring to FIG. 2, there is shown the results of separation from the principal component analysis for chemicals of acetic acid, acetone, hexane, toluene, and water, where their resistance and reactance data were obtained at frequencies 502, 550, 600, 651, 700, 750, 801, 850, 901, 949 and 1,000 KHz according to the present invention. Each chemical was repeatedly measured three times in accordance with the procedure described above. During data analysis applying PCA, the raw data matrix of change of resistance and reactance was autoscaled and normalized to the length one before further processing. The results indicate that impedance and its components can be used to identify chemicals.

It is understood that the application of the above specified frequencies is only for illustration of effectiveness for the present invention. It is not intended here to limit other frequencies within the frequency ranges in applications.

Furthermore, it can be understood from the above experimental results that, instead of identifying analytes in fluids from multiple frequency detection, the present invention can also be used to detect presence of analytes of interests with a single frequency application. For example, in GC chemical analysis, chemicals are eluted separately out of the column by a carrier gas (usually hydrogen, or helium, or nitrogen). Each chemical can be detected in presence because of different AC electrical properties from the carrier gas and chemicals at the applied frequency. As another example, detection of known flammable gases such as methane is critical for safe operation in mine industry. Detection of such gases can be achieved at a pre-selected frequency with application of core technologies in the present invention.

Figure 7A:
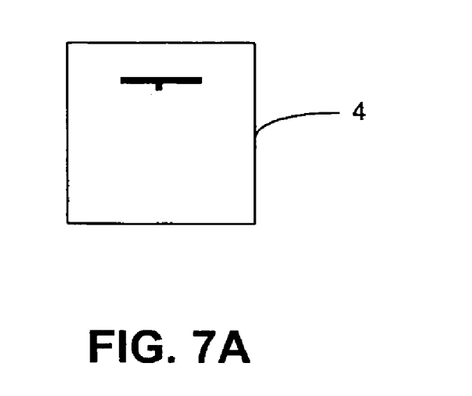
FIG. 7A shows a schematic diagram to show a different configuration 4 to form a single sensor where an electrode acting as a first electrode, and electrically conductive structure member, such as a sidewall acting as a second electrode.
Figure 7B:
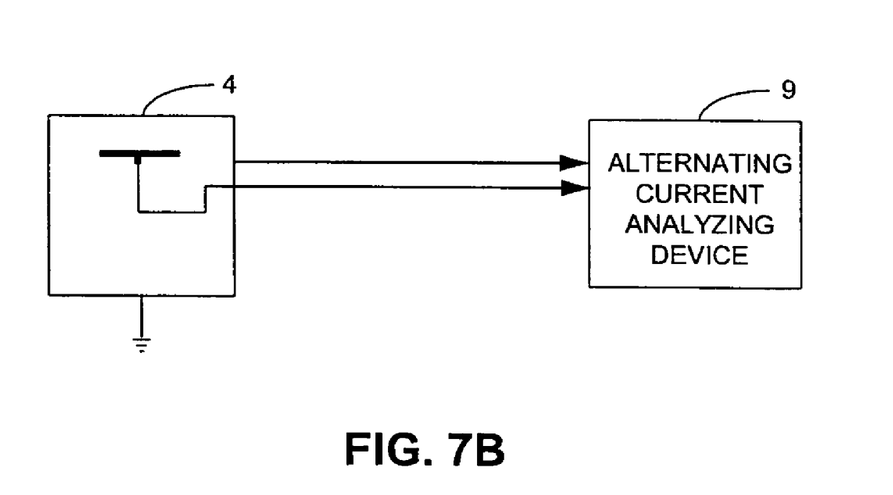
FIG. 7B shows a sidewall is properly grounded in connection of the sensor 4 to the alternating current analyzing device 9.

In addition, referring to FIGS. 7A and 7B, in the single sensor according to the present invention, the two electrodes may be formed in many ways. For example, when a first electrode is positioned at a location close to a sidewall of a container made of electrically conductive material which is properly grounded, then the sidewall of the container may serve as a second electrode. The fluid to be tested can be directed to pass through the gap between the first electrode and the sidewall of the container which functions as the second electrode.

The present invention has many advantages. It utilizes a single analytical sensor to generate a spectrum of chemical signals. The small size which results in low power consumption on sensor temperature regulation and small volume requirement also allows the implementation of a dual sensing detection strategy which, in addition to the analytical sensor, incorporates a reference sensor with identical configurations. With this dual sensor configuration, the effects of background subjects such as humidity levels, or other factors such as the aging effect for polymer films and changes in testing responses induced by temperature variations, can also be eliminated.

The present invention sensor and method also operate within a low frequency range between 10 KHz and 1 MHz. The low energy consumption of the present invention sensor further allows the use of temperature programming to improve the detection and identification of the analytes. Applying the electric impedance method, the present invention provides capability to use all types of adsorbents, including organic, inorganic, and metal materials. In addition, the present invention sensor device is low cost to produce, compact in size, portable, and easy to use.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

The present invention has been described in considerable detail in order to comply with the patent laws by providing full public disclosure of at least one of its forms. However, such detailed description is not intended in any way to limit the broad features or principles of the present invention.

Although the above invention is described in some detail by way of illustration and example for purposes of clarity of understanding, it is apparent to those of ordinary skill in the art in light of the teaching of this invention that many changes and modifications may be made thereto without departing from the scope of the appended claims.

What is claimed is:

1. A sensor, comprising:
   a. an analytical sensor comprises first and second electrodes that are electrically separated by a non-conductive material;
   b. said analytical sensor is electrically connected to an alternating current (AC) analyzing device, wherein said AC analyzing device applies various frequencies of AC signals to said analytical sensor;
   c. said analytical sensor is brought into contact with a first fluid containing an analyte;
   d. AC related electrical properties are detected for said analytical sensor when contacted by said first fluid containing said analyte according to said applied various frequencies of said AC signals, wherein said electrical properties are detected at each of said applied various frequencies; and
   e. said detected AC related electrical properties are used for identification of said analyte according to frequencies in a selected subgroup of said applied various frequencies, wherein said frequencies in said selected subgroup include both higher and lower frequencies of said applied various frequencies.

2. The sensor as claimed in claim 1, wherein said AC related electrical properties include impedance, resistance, reactance, phase angle, voltage and current.

3. The sensor as claimed in claim 1, further comprising a conductive material that is positioned between said first and second electrodes of said analytical sensor.

4. The sensor as claimed in claim 1, wherein said non-conductive material is selected from the group consisting of polymer, polymer inorganic material composite, molecular sieves, silica gel, alumina, porous carbon, and calcium carbonate particles, composite of palladium particles and inorganic materials, or composite of palladium particles and polymer, polymer modified porous ceramic particles including porous alumina, or polymer modified porous silica, and polymer modified porous glass beads.

5. The sensor as claimed in claim 1, further comprising means for implementing a temperature programming technique.

6. The sensor as claimed in claim 1, further comprising:
   a. said analytical sensor is brought into contact with a second fluid which is identical to said first fluid but does not contain any analyte;
   b. AC related electrical properties are detected for said analytical sensor when contacted by said second fluid according to said applied various frequencies of said AC signals, wherein said electrical properties are detected at each of said applied various frequencies;
   c. combined AC related electrical properties of said analyte are obtained by combining the respective AC related electrical properties of said analytical sensor when contacted by said first fluid containing said analyte with the respective AC related electrical properties of said analytical sensor when contacted by said second fluid, and
   d. said combined AC related electrical properties are used for identification of said analyte according to frequencies in a selected subgroup of said applied various frequencies, wherein said frequencies in said selected subgroup include both higher and lower frequencies of said applied various frequencies.

7. The sensor as claimed in claim 1, further comprising an odorant as said analyte.

8. The sensor as claimed in claim 1, wherein said analyte is tested for medical diagnoses.

9. The sensor as claimed in claim 1, further comprising a reference sensor that is identical to said analytical sensor, wherein said reference sensor is used for correcting background effect that includes the group comprising electrical property variations caused by temperature variations, polymer film aging effect and effect of humidity levels.

10. The sensor as claimed in claim 1, further comprising at least two of said analytical sensor.

11. A fluid sensor, comprising:
    a. an analytical sensor which comprises first and second electrodes that are electrically separated by an air gap;
    b. said analytical sensor is electrically connected to an alternating current (AC) analyzing device in a test, wherein said AC analyzing device applies a single frequency of AC signal to said analytical sensor during a duration of said test;
    c. a fluid which flows and contains at least one analyte is tested by said analytical sensor during said duration of said test, said at least one analyte that mixes with a fraction of said flowing fluid is carried by said flowing fluid to said analytical sensor, said flowing fluid continuously comes into contact with said analytical sensor, and said at least one analyte comes into contact with said analytical sensor at a point in time when said at least one analyte passes said analytical sensor; and
    d. one AC related electrical property is detected for said analytical sensor when contacted by said at least one analyte according to said applied single frequency of said AC signal, wherein said detected AC related electrical property is used for detection of said at least one analyte present in said flowing fluid.

12. The fluid sensor as claimed in claim 11, wherein said AC related electrical property includes impedance, resistance, reactance, phase angle, voltage and current.

13. The fluid sensor as claimed in claim 11, wherein said flowing fluid which contains said at least one analyte flows through a chromatographic column.

14. The fluid sensor as claimed in claim 11, wherein said flowing fluid is selected from the group consisting of hydrogen, nitrogen and helium gases.

15. The fluid sensor as claimed in claim 11, further comprising means for implementing a constant temperature technique that is applied to said analytical sensor.

16. The fluid sensor as claimed in claim 11, further comprising:
    a. one AC related electrical property is detected for said analytical sensor when contacted by said flowing fluid at another point in time;
    b. a combined AC related electrical property is obtained for said at least one analyte by combining said one AC related electrical property of said analytical sensor when contacted by said flowing fluid at said another point in time with said one AC related electrical property of said analytical sensor when contacted by said at least one analyte; and
    c. said combined AC related electrical property according to said applied single frequency is used for detection of said at least one analyte present in said flowing fluid.

17. The fluid sensor as claimed in claim 11, further comprising:
    a. said AC analyzing device repeatedly applies various frequencies of AC signals to said analytical sensor during said duration of said test;
    b. AC related electrical properties are detected for said analytical sensor when contacted by said at least one analyte according to said applied various frequencies of said AC signals, wherein said electrical properties are detected at each of said applied various frequencies, AC electrical properties are detected for said analytical sensor when contacted by said flowing fluid at another point in time according to said applied various frequencies, wherein said electrical properties are detected at each of said applied various frequencies;

c. combined AC related electrical properties are obtained for said at least one analyte by combining the respective AC related electrical properties of said analytical sensor when contacted by said flowing fluid at said another point in time with the respective AC related electrical properties of said analytical sensor when contacted by said at least one analyte; and d. said combined AC related electrical properties are used for identification of said at least one analyte according to frequencies in a selected subgroup of said applied various frequencies, wherein said frequencies in said selected subgroup include both higher and lower frequencies of said applied various frequencies.

18. The fluid sensor as claimed in claim 11, wherein said flowing fluid contains at least two analytes.

19. A gas sensor, comprising:

a. an analytical sensor which comprises first and second electrodes that are electrically separated by a first composite material comprising filler and palladium metal that does not contain palladium oxide;

b. said analytical sensor is electrically connected to an alternating current (AC) analyzing device, wherein said AC analyzing device applies a single frequency of AC signal to said analytical sensor;

c. said analytical sensor is brought into contact with a first gas containing an analyte that is a gaseous hydrogen, wherein said palladium metal selectively absorbs said gaseous hydrogen;

d. one AC related electrical property is detected for said analytical sensor when contacted by said first gas containing said gaseous hydrogen according to said applied single frequency of said AC signal; and e. said AC related electrical property is used for detection of said gaseous hydrogen.

20. The gas sensor as claimed in claim 19, wherein said AC related electrical properties include impedance, resistance, reactance, phase angle, voltage and current.

21. The gas sensor as claimed in claim 19, further comprising means of implementing a temperature programming technique to said analytical sensor.

22. The gas sensor as claimed in claim 19, further comprising:

a. a reference sensor which is identical to said analytical sensor has third and fourth electrodes that are electrically separated by a second composite material that is identical to said first composite material;

b. said reference sensor is electrically connected to said AC analyzing device, wherein said AC analyzing device applies said single frequency of said AC signal to said reference sensor;

c. said reference sensor is brought into contact with a second gas which is identical to said first gas but does not contain any analyte;

d. one AC related electrical property is detected for said reference sensor when contacted by said second gas according to said applied single frequency of said AC signal, and a combined AC related electrical property is obtained for said gaseous hydrogen by combining said one AC related electrical property of said reference sensor with said one AC related electrical property of said analytical sensor; and e. said combined AC related electrical property is used for detection of said gaseous hydrogen.

23. The gas sensor as claimed in claim 19, wherein said filler is selected from the group consisting of organic and inorganic materials.

24. The gas sensor as claimed in claim 19, further comprising:

a. said analytical sensor is brought into contact with a second gas which is identical to said first gas but does not contain any analyte;

b. one AC related electrical property is detected for said analytical sensor when contacted by said second gas according to said applied single frequency of said AC signal;

c. a combined AC related electrical property is obtained for said gaseous hydrogen by combining said one AC related electrical property of said analytical sensor when contacted by said first gas containing said gaseous hydrogen with said one AC related electrical property of said analytical sensor when contacted by said second gas; and d. said combined AC related electrical property is used for detection of said gaseous hydrogen.

25. A sensor, comprising:

a. an analytical sensor comprises first and second electrodes that are electrically separated by a non-conductive material;

b. said analytical sensor is brought into contact with a fluid containing an analyte;

c. means, applied by various frequencies of AC signals, for detecting AC related electrical properties of said analytical sensor when contacted by said fluid containing said analyte according to said applied various frequencies, wherein said electrical properties are detected at each of said applied various frequencies; and d. said detected AC related electrical properties are used for identification of said analyte according to frequencies in a selected subgroup of said applied various frequencies, wherein said frequencies in said selected subgroup include both higher and lower frequencies of said applied various frequencies.

26. A fluid sensor, comprising:

a. an analytical sensor which comprises first and second electrodes that are electrically separated by an air gap;

b. a fluid which flows and contains at least one analyte is tested by said analytical sensor in a test during a duration of said test, said at least one analyte that mixes with a fraction of said flowing fluid is carried by said flowing fluid to said analytical sensor, said flowing fluid continuously comes into contact with said analytical sensor, and said at least one analyte comes into contact with said analytical sensor at a point in time when said at least one analyte passes said analytical sensor; and c. means, applied by a single frequency of AC signal during said duration of said test, for detecting one AC related electrical property of said analytical sensor when contacted by said at least one analyte according to said applied single frequency of said AC signal, wherein said detected AC related electrical property is used for detection of said at least one analyte present in said flowing fluid.

* * * * *